United States Patent [19]
Erskine

[11] Patent Number: 5,824,001
[45] Date of Patent: Oct. 20, 1998

[54] RADIALLY VENTED FLASHBACK CHAMBER AND PLUG ASSEMBLY

[75] Inventor: Timothy J. Erskine, Sandy, Utah

[73] Assignee: Becton Dickinson and Company, Franklin Lakes, N.J.

[21] Appl. No.: 662,718

[22] Filed: Jun. 10, 1996

[51] Int. Cl.⁶ ..................................................... A61M 5/00
[52] U.S. Cl. ...................... 604/158; 604/122; 604/126; 604/168; 604/159
[58] Field of Search .................... 604/164, 167, 604/158, 159, 195, 122, 126, 168, 411

[56] References Cited

U.S. PATENT DOCUMENTS

| | | | |
|---|---|---|---|
| 3,670,729 | 6/1972 | Bennet et al. | 604/164 X |
| 4,149,535 | 4/1979 | Volder | 604/164 X |
| 4,682,980 | 7/1987 | Suzuki | 604/122 |
| 4,935,008 | 6/1990 | Lewis, Jr. | 604/164 X |
| 5,032,116 | 7/1991 | Peterson et al. | 604/168 |
| 5,053,014 | 10/1991 | Van Heugten | 604/167 |
| 5,078,689 | 1/1992 | Keller | 604/164 X |
| 5,129,884 | 7/1992 | Dysarz | 604/164 |
| 5,312,355 | 5/1994 | Lee | 604/164 X |
| 5,484,416 | 1/1996 | Gittings | 604/164 |
| 5,501,675 | 3/1996 | Erskine | 604/164 X |

FOREIGN PATENT DOCUMENTS

| | | |
|---|---|---|
| 0 353 905 A1 | 2/1990 | European Pat. Off. . |
| 0 495 497 A1 | 7/1992 | European Pat. Off. . |
| 0 653 220 A1 | 5/1995 | European Pat. Off. . |
| 0 655 259 A2 | 5/1995 | European Pat. Off. . |

*Primary Examiner*—Richard J. Apley
*Assistant Examiner*—Benjamin K. Koo
*Attorney, Agent, or Firm*—Eric M. Lee

[57] ABSTRACT

A radially vented flashback chamber and plug assembly includes a plug seated in the proximal end of a flashback chamber. In one embodiment of this invention, the flashback chamber has an open proximal end and the plug has a closed proximal end, an open distal end, a lumen extending proximally from the open distal end, and a radially extending passageway located distal of the closed proximal end in communication with the lumen. A porous material is inserted into the lumen at the juncture between the lumen and the radially extending passageway to prevent blood leakage from the flashback chamber. One or more rings are located around the periphery of the plug proximal of the radially extending passageway to create a fluid tight seal between the flashback chamber and the barrel in which the flashback chamber is housed.

5 Claims, 4 Drawing Sheets

5,824,001

RADIALLY VENTED FLASHBACK CHAMBER AND PLUG ASSEMBLY

BACKGROUND OF THE INVENTION

This invention relates a radially vented flashback chamber and plug assembly. More particularly, this invention relates to a flashback chamber plug seated in the proximal end of a flashback chamber that allows radial venting of the flashback chamber. This invention may be used in conjunction with an intravenous (IV) catheter.

IV catheters are designed to infuse normal intravenous solutions, including antibiotics and other drugs, into a patient. These catheters are also used to withdraw blood from the patient for normal blood-gas analysis as well as other blood work. In order to insert an IV catheter into a patient, an introducer needle is used. The needle is typically stainless steel and is hollow. Its distal tip is ground to a sharp tip for easy insertion into the patient. The catheter is also hollow and is initially located coaxially around the introducer needle in an "over the needle" arrangement. Thus, the catheter rides with the needle through the patient's skin, tissue and into the patient's vein.

During the insertion process, it is desirable for the clinician to be able to determine if the tip of the needle and catheter are properly located in the patient's vein. This determination can be made because the proximal end of the needle is typically connected to a hollow transparent or translucent flashback chamber. Thus, when the tip of the needle and catheter enter the patient's vein, blood will flow through the needle into the flashback chamber for observation by the clinician.

In order for the blood to be able to flow through the needle into the flashback chamber, the proximal end of the flashback chamber must be vented. This allows the air in the flashback chamber to exit therefrom as blood enters the flashback chamber. However, the proximal end of the flashback chamber should not allow blood to leak therefrom. Blood leakage is undesirable because of the possibility of the transmission of blood-borne diseases, such as AIDS and hepatitis, between the patient and the clinician.

In view of the advent of such blood-borne diseases, there has been great concern over the immediate disposal of needles after use. If a needle has been used to place a catheter in the vein of an AIDS infected person, the needle is a vehicle for the transmission of the disease. Thus, it is extremely important for a clinician to properly dispose of the needle after use to avoid a needle stick with a contaminated needle. Unfortunately, in certain medical environments, such as emergency situations, needlesticks with a contaminated needle can occur if the contaminated needle is not somehow covered immediately after use. Much effort has been directed to developing an introducer needle assembly that can be shielded after use to minimize the possibility of an accidental needlestick with a contaminated needle. One such assembly is a spring activated needle retraction system such as disclosed in U.S. Pat. No. 4,747,831, the disclosure of which is hereby incorporated by reference.

Such a spring activated needle retraction system generally works for its intended purpose in that it provides a simple mechanism that allows the clinician to shield a needle immediately after use. However, the device disclosed in U.S. Pat. No. 4,747,831 could be improved. In such a spring activated needle retraction system, the flashback chamber, to which the needle is attached, is retracted into a barrel with a certain velocity. Thus the air in the space between the flashback chamber and the proximal end of the barrel will be displaced through the vent located in the proximal end of the flashback chamber and through the needle upon retraction of the flashback chamber. This could result in blood located in the flashback chamber being expelled through the needle and out the distal end of the needle upon retraction.

SUMMARY OF THE INVENTION

It is therefore an object of this invention to provide a flashback chamber and plug assembly that will vent air but not blood from the flashback chamber.

It is another object of this invention to provide a flashback chamber and plug assembly that will minimize the chance that blood will be expelled from the flashback chamber through the distal end of the needle when the flashback chamber and needle are retracted into the barrel.

The flashback chamber and plug assembly of this invention allows air to be vented from the flashback chamber only in a radial fashion. One or more rings are located around the periphery of the flashback chamber and plug assembly proximal of the radially extending passageways. This creates a fluid tight seal between the interior of the barrel and the exterior of the flashback chamber. In this way, blood can not be expelled through the needle when the flashback chamber and plug assembly and the needle are retracted into the barrel. In one embodiment of the invention, the flashback chamber has an open proximal end with a plug fitted therein. The plug includes a body with a closed proximal end, an open distal end, a lumen extending from the open distal end to at least one radially extending passageway extending from the lumen to the side of the plug adjacent to the proximal end. A porous material is located in the lumen at the junction between the lumen and the radially extending passageway to prevent blood leakage. The open distal end of the plug is placed in the open proximal end of a flashback chamber to allow air but not blood to be vented from the plug. The proximal end of the plug preferably includes one or more rings about its circumference to create a fluid tight seal between the barrel and the plug.

In an alternate embodiment, the flashback chamber has an open proximal end as well as a radially extending passageway adjacent to the open proximal end. A solid plug closes the open proximal end while porous material is used to cover the radially extending passageway. In still another embodiment, the flashback chamber has a closed proximal end and a radially extending passageway that is covered by a porous material.

BRIEF DESCRIPTION OF THE DRAWINGS

The above and other objects and advantages of the invention will be apparent from the detailed description and drawings in which like parts are referred to by like numbers throughout, and in which.

DETAILED DESCRIPTION OF THE INVENTION

Figure 1:
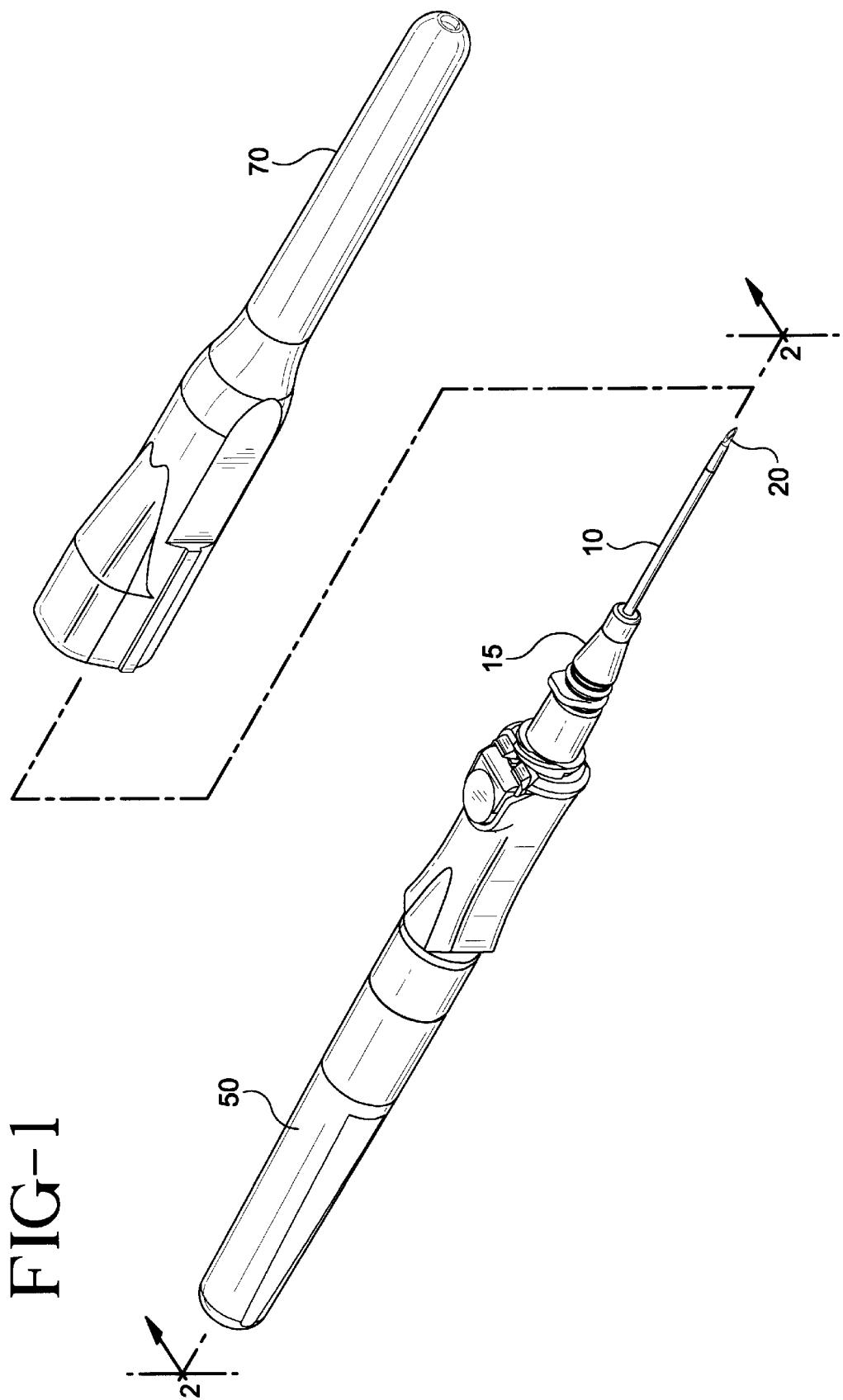
FIG. 1 is a perspective view of a catheter and spring activated introducer needle assembly incorporating the flashback chamber and plug assembly of this invention.

FIG. 1 shows a catheter and introducer needle assembly incorporating the principles of this invention. Although this invention is particularly applicable to a catheter and introducer needle assembly that incorporates a spring activated needle retraction system to shield the sharp distal tip of the needle after use, the invention may also be used for other catheter and introducer needle assemblies.

The catheter 10 is a tube typically formed from a Teflon or polyurethane material. The distal end of catheter 10 is tapered to facilitate insertion into a patient. The proximal end of catheter 10 is affixed to a catheter hub 15 which is formed to be connected to an IV tubing set (not shown) or other medical device such as a valve or a syringe.

Figure 2:
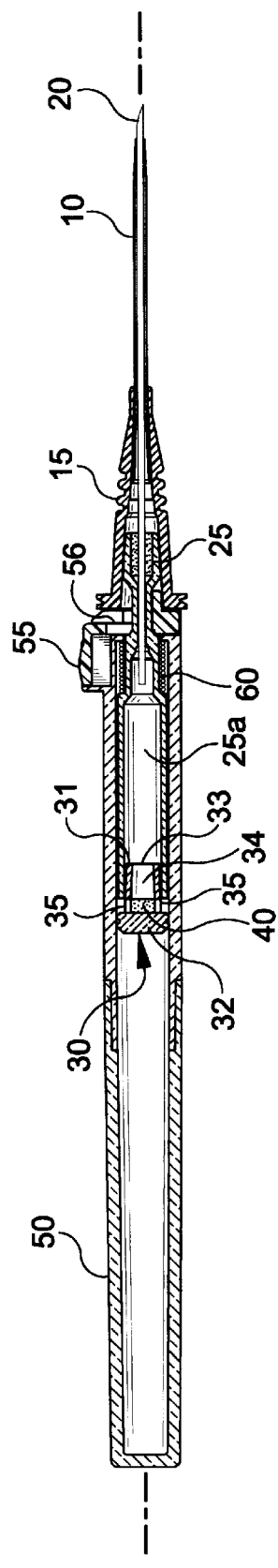
FIG. 2 is a cross sectional view taken along line 2—2 of FIG. 1 of the catheter and spring activated introducer needle assembly incorporating the flashback chamber and plug assembly of this invention.
Figure 3:
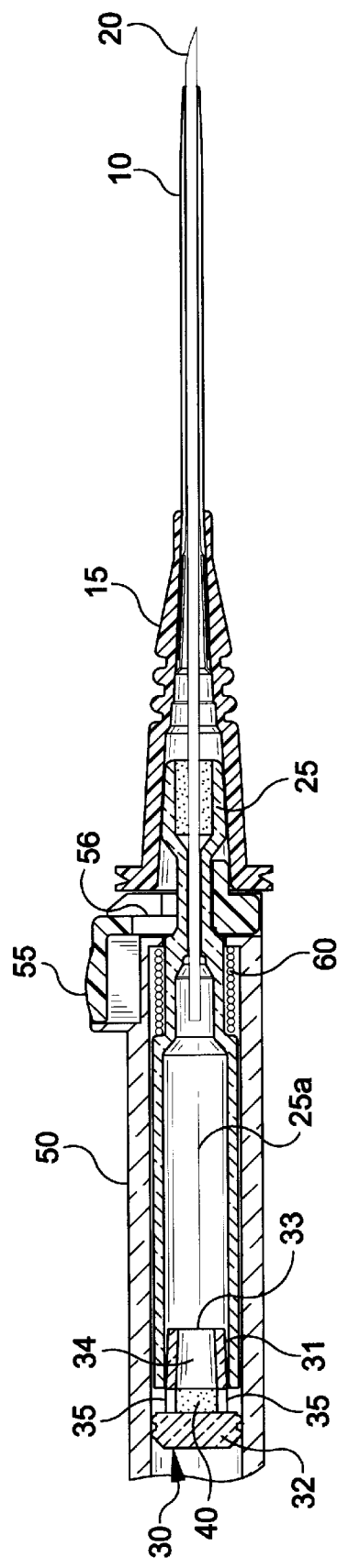
FIG. 3 is an enlarged view of the distal portion of FIG. 2.
Figure 4:
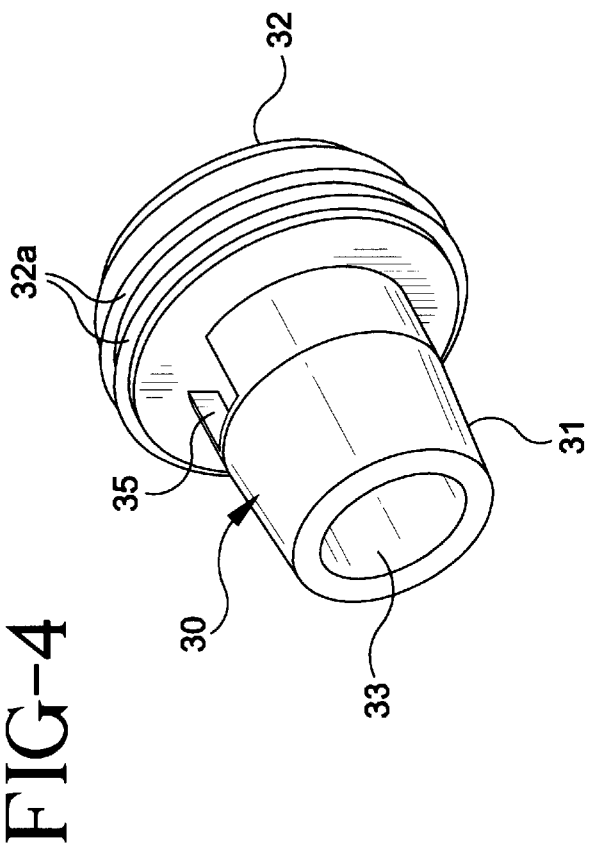
FIG. 4 is a perspective view of a preferred embodiment of the plug of this invention.

A hollow introducer needle 20 is initially located within catheter 10 with the distal end of needle 20 extending slightly beyond the distal end of catheter 10. The distal end of needle 20 is sharp to facilitate insertion into a patient. A cover 70 may be placed over the distal portion of the catheter and introducer needle assembly to shield the sharp distal tip of needle 20 to avoid accidental needlesticks and to maintain the sterility of catheter 10 and needle 20. The proximal end of needle 20 is affixed to a hub 25 that typically includes a flashback chamber 25a. Flashback 25a is preferably transparent or translucent to enable the clinician to observe blood therein when the distal end of the needle enters the patient's vein. In the embodiment shown in FIGS. 2–4, the proximal end of flashback chamber 25a is open.

Inserted into the open proximal end of flashback chamber 25a is plug 30. Plug 30 includes a distal portion 31 and a proximal portion 32. Distal portion 31 has a smaller outside diameter than proximal portion 32. Preferably distal portion 31 is tapered such that plug 30 will frictionally remain in place when inserted in the open proximal end of flashback chamber 25a. In addition, distal portion 31 defines a distal opening 33, a lumen 34 and at least one radially extending passageway 35 therein. Radially extending passageway 35 should be located in a portion of distal portion 31 that has a larger outer diameter than the inner diameter of the proximal end of flashback chamber 25a. This ensures that radially extending passageway 35 will be in communication with the exterior of flashback chamber 25a when plug 30 is inserted in the open proximal end of flashback chamber 25a. Proximal portion 32 of plug 30 is closed. Preferably, plug 30 includes one or more gaskets or rings 32a. See FIG. 4. These rings 32a which are located proximal of radially extending passageway 35, create a fluid tight seal between barrel 50 and flashback chamber 25a. Rings 32a may be integrally formed in proximal portion 32 of plug 30 or they may be separately formed and attached to proximal portion 32 of plug 30.

Inserted in plug 30 is a material 40 that is impervious to liquid but pervious to gas. Material 40 is preferably made from a porous polymeric material that is press fit into plug 30 to remain in place. Material 40 is located in lumen 34 at the juncture between lumen 34 and radially extending passageway 35 to prevent blood from being expelled through radially extending passageway 35. The porous polymeric material used to form material 40 is preferably a low density polyethylene available commercially under the trade name POREX from Porex Materials Corporation. Alternatively, a thin perforated or slit liquid impervious material can be placed over radially extending passageway 35.

Needle 20, flashback chamber 25a, plug 30 and material 40 are located in barrel 50. Barrel 50 is generally hollow and is of sufficient length to allow needle 20, flashback chamber 25a, and plug 30 to be retracted into barrel 50 so that the sharp distal tip of needle 20 is safely housed in barrel 50. A spring 60 is located about needle 20 and hub 25 and extends between flashback chamber 25a and the distal end of barrel 50. Spring 60 provides the biasing force to retract needle 20 into barrel 50 after needle 20 has been used to properly place catheter 10 into a patient.

An activation latch 55 extends into barrel 50 via a slot formed in barrel 50 adjacent to the distal end. Activation latch 55 includes a keyhole shaped opening 56 that allows needle 20 and hub 25 to extend through activation latch 55. When activation latch 55 is "up" in the non-activated position, see FIGS. 2, 3, 5 and 6, the smaller portion of keyhole shaped opening 56 is in communication with the interior of barrel 50. In this position, the smaller opening of keyhole shaped opening 56 engages hub 25 and holds hub 25 adjacent to the distal end of barrel 50 against the force of spring 60. When activation latch 55 is moved "down" to the activated position, the larger opening of keyhole shaped opening 56 no longer engages hub 25 so that spring 60 can force hub 25 to the proximal end of barrel 50 and withdraw the sharp distal tip of needle 20 into barrel 50.

Figure 5:
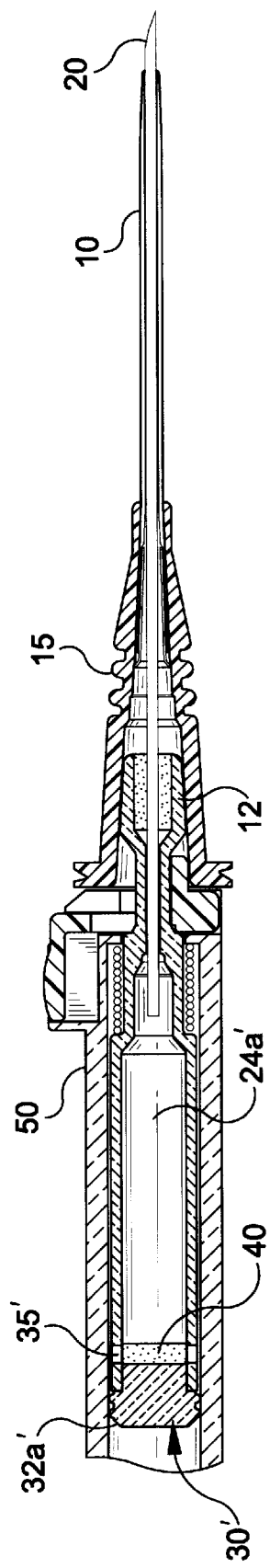
FIG. 5 is a cross sectional view similar to FIG. 3, but showing an alternate embodiment of the flashback chamber and plug assembly of this invention.

In an alternate embodiment shown in FIG. 5, flashback chamber 25a' has an open proximal end and at least one radially extending passageway 35' formed therein. Plug 30' is solid and is fitted into the open proximal end of flashback chamber 25a'. Material 40 that is impervious to liquid but pervious to gas, such as low density polyethylene, is located adjacent to radially extending passageway 35' to allow air but not blood to be vented from flashback chamber 25a'. One or more rings 32a' are located around the periphery of plug 35' proximal of radially extending passageway 35' to create a fluid tight seal between plug 30' and barrel 50.

Figure 6:
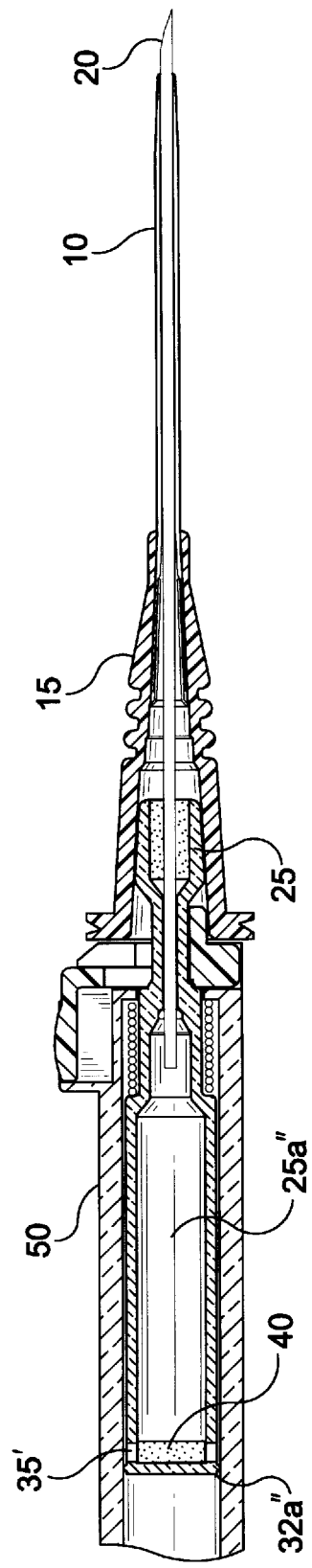
FIG. 6 is a cross-sectional view similar to FIG. 3, but showing a further alternate embodiment of the flashback chamber and plug assembly of this invention.

In still another embodiment shown in FIG. 6, flashback chamber 25a" has a closed proximal end and a radially extending passageway 35' that is covered by a material 40 that is impervious to liquid but pervious to gas such as a low density polyethylene. One or more rings 32a" are located around the periphery of flashback chamber 25a" proximal of radially extending passageway 35' to create a fluid tight seal between flashback chamber 25a" and barrel 50.

In all of the embodiments of this invention, any blood that may be contained in flashback chamber 25a will not be expelled therefrom when needle 20 is being retracted into barrel 50. This is because the air in the space between flashback chamber 25a and the proximal end of barrel 50 can not be expelled through flashback chamber 25a since there is no fluid flow path from this space to the interior of flashback chamber 25a. The fluid tight seal between flashback chamber 25a and barrel 50 created by rings 32a ensures that this is the case. And the annular space between the exterior of flashback chamber 25a and the interior of barrel 50 provides a flow path for air expelled from flashback chamber 25a when blood enters flashback chamber 25a.

Thus, it is seen that a flashback chamber and plug assembly is provided that permits air to be vented from the flashback chamber but not blood and minimizes the chances that blood will be expelled from the flashback chamber through the needle when the flashback chamber and the needle are retracted into the barrel.

I claim:

1. A catheter and introducer needle assembly, comprising:

a catheter having a catheter hub;

a generally hollow barrel having a proximal end and a distal end;

a needle having a sharp distal tip and a proximal end disposed in the catheter;

a needle hub affixed adjacent to the proximal end of the needle having a periphery, an open proximal end and movably disposed in the barrel;

a plug disposed in the open proximal end of the needle hub, the plug having a body portion having an open distal end, a closed proximal end, a lumen extending from the open distal end to a position distal of the closed proximal end and at least one radially extending passageway located distal of the closed proximal end in fluid communication with the lumen;

a material impervious to liquid but pervious to gas located in the lumen at the juncture between the lumen and the radially extending passageway;

a spring disposed about the needle and extending between the needle hub and the distal end of the barrel; and an activation latch movably mounted adjacent to the distal end of the barrel and adapted for selective engagement with the needle hub to hold the needle hub adjacent to the distal end of the barrel against the bias of the spring such that the needle extends beyond the distal end of the barrel and through the catheter with the catheter hub adjacent to the distal end of the barrel.

2. The catheter and introducer needle assembly of claim 1 further comprising at least one ring located about the periphery of the plug.

3. The catheter and introducer needle assembly of claim 2 wherein the at least one ring is proximal of the radially extending passageway.

4. The catheter and introducer needle assembly of claim 1 wherein the material is porous.

5. The catheter and introducer needle assembly of claim 4 wherein the material is a low density polyethylene.

* * * * *